United States Patent
Cilurzo et al.

(10) Patent No.: US 11,123,287 B2
(45) Date of Patent: Sep. 21, 2021

(54) ORODISPERSIBLE FILMS HAVING QUICK DISSOLUTION TIMES FOR THERAPEUTIC AND FOOD USE

(71) Applicant: PHARMAFILM S.R.L., Gaggiano (IT)

(72) Inventors: Francesco Cilurzo, Gaggiano (IT); Maurizio Di Grigoli, Gaggiano (IT); Paola Minghetti, Gaggiano (IT); Stefania Pagani, Gaggiano (IT)

(73) Assignee: PHARMAFILM S.R.L., GAGGIANO (IT)

( * ) Notice: Subject to any disclaimer, the term of this patent is extended or adjusted under 35 U.S.C. 154(b) by 81 days.

(21) Appl. No.: 14/430,255

(22) PCT Filed: Sep. 26, 2013

(86) PCT No.: PCT/IB2013/058882
§ 371 (c)(1),
(2) Date: Mar. 23, 2015

(87) PCT Pub. No.: WO2014/049548
PCT Pub. Date: Apr. 3, 2014

(65) Prior Publication Data
US 2015/0231065 A1 Aug. 20, 2015

(30) Foreign Application Priority Data
Sep. 28, 2012 (IT) .............................. MI2012a001628

(51) Int. Cl.
| | |
|---|---|
| *A61K 9/00* | (2006.01) |
| *A61Q 11/00* | (2006.01) |
| *A23L 33/15* | (2016.01) |
| *A61K 8/81* | (2006.01) |
| *A61K 45/06* | (2006.01) |
| *A61K 47/32* | (2006.01) |

(52) U.S. Cl.
CPC ............ *A61K 9/0056* (2013.01); *A23L 33/15* (2016.08); *A61K 8/8129* (2013.01); *A61K 9/006* (2013.01); *A61K 45/06* (2013.01); *A61K 47/32* (2013.01); *A61Q 11/00* (2013.01)

(58) Field of Classification Search
CPC .. A61K 9/0053; A61K 2800/92; A61K 9/006; A61K 9/0056; A61K 9/2846; A61Q 11/00
See application file for complete search history.

(56) References Cited

U.S. PATENT DOCUMENTS

| | | | | |
|---|---|---|---|---|
| 6,339,121 | B1 * | 1/2002 | Rafailovich | ............... C08J 5/18 524/445 |
| 7,132,113 | B2 * | 11/2006 | Zerbe | .................... A23L 1/0067 424/400 |
| 2004/0076658 | A1 | 4/2004 | Hoess et al. | |
| 2004/0247646 | A1 * | 12/2004 | Ivory | ...................... A61K 8/027 424/439 |
| 2005/0281757 | A1 * | 12/2005 | Ibrahim | ............... A61K 8/0208 424/49 |
| 2008/0213343 | A1 * | 9/2008 | Obermeier | ........... A61K 9/0056 424/443 |
| 2009/0017085 | A1 * | 1/2009 | Cilurzo | .................. A61K 9/006 424/409 |
| 2010/0178306 | A1 * | 7/2010 | Kolter | .................. A61K 9/0056 424/400 |
| 2011/0262520 | A1 | 10/2011 | Dormady et al. | |
| 2013/0122072 | A1 * | 5/2013 | Anastasiou | ............... A23G 1/32 424/401 |

FOREIGN PATENT DOCUMENTS

| | | | | |
|---|---|---|---|---|
| WO | 0009095 | | 2/2000 | |
| WO | WO-2011048563 | A2 * | 4/2011 | ........... A61K 9/0056 |
| WO | WO-2017009754 | A1 * | 1/2017 | ........... A61K 31/137 |

OTHER PUBLICATIONS

Singh et al. Optimization and Evaluation of Desloratadine Oral Strip: An Innovation in Paediatric Medication. 2013. Hindawi Publishing Corporation. vol. 2013. 9 pages. (Year: 2013).*
International Preliminary Report on Patentability of PCT/IB2013/058882 dated Apr. 9, 2015.
International Search Report of PCT/IB2013/058882 dated Mar. 4, 2014.
Written Opinion of PCT/IB2013/058882 dated Mar. 4, 2014.

* cited by examiner

*Primary Examiner* — Tracy Liu
(74) *Attorney, Agent, or Firm* — Silvia Salvadori, P.C.; Silvia Salvadori

(57) ABSTRACT

The present invention concerns an orodispersible self-supporting film free from hydrocolloids comprising: a) a film-forming substance consisting of a maltodextrin in an amount comprised between 40 and 80% by weight; b) a plasticizer in an amount comprised between 15 and 55% by weight; e) a surfactant System in an amount comprised between 0.5 and 6% by weight; d) an active ingredient for food or therapeutic use in an amount between 0.05 and 30% by weight, characterised in that it contains a homopolymer or a copolymer of vinyl acetate in a quantity comprised between 2 and 10% by weight where the percentages are calculated on the total weight of said film.

26 Claims, 2 Drawing Sheets

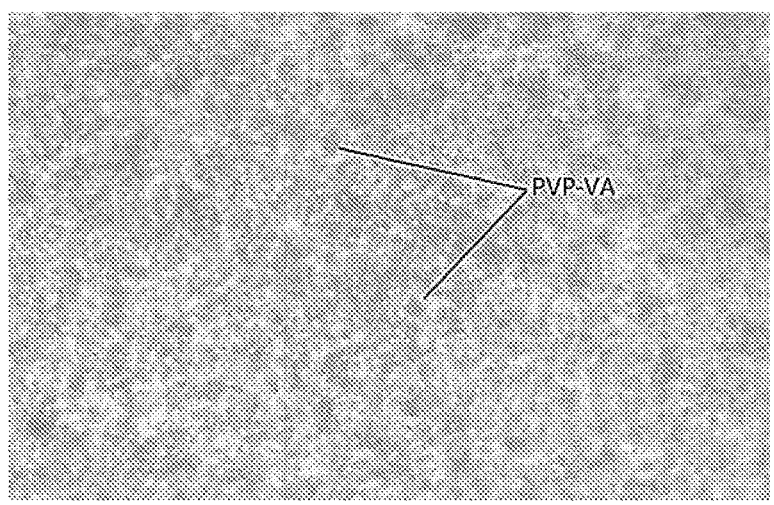
Figure 1: Image of film F10 containing 10% of PVP-VA captured using optical transmission microscope

Figure 2: Image of film F6 containing 2% of PVP-VA captured using optical transmission microscope.
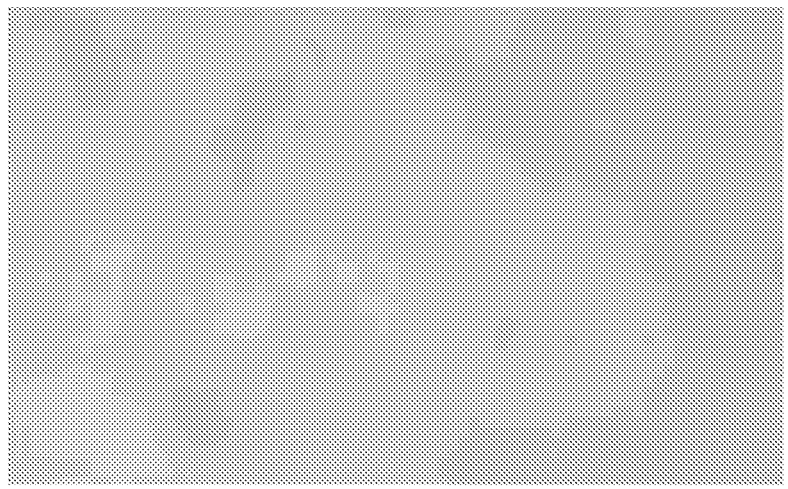
Figure 3: Image of film prepared according Ibrahim patent captured using optical transmission microscope.

ORODISPERSIBLE FILMS HAVING QUICK DISSOLUTION TIMES FOR THERAPEUTIC AND FOOD USE

FIELD OF THE INVENTION

This application is a U.S. national stage of PCT/IB2013/058882 filed on 26 Sep. 2013, which claims priority to and the benefit of Italian Application No. MI2012A001628, filed on 28 Sep. 2012, the contents of which are incorporated herein by reference in their entirety.

The present invention concerns orodispersible self supporting films having quick dissolution times for therapeutic and food use.

STATE OF THE ART

Orodispersible self supporting films for releasing active ingredients for therapeutic or food use have been known for a long time and are available on the market.

These films disintegrate quickly in the mouth releasing the active ingredient.

Many of the films known at the state of the art use pullulan as the film forming component which is, however, an ingredient that is expensive and difficult to find.

It has thus been attempted to replace pullulan with less expensive ingredients that are, in any case, capable of maintaining the properties like their quick dissolution times, mouth freshness, marked aroma, and simplicity of preparation.

US2003011259 describes a film having quick dissolution times containing maltodextrin and hydrocolloids, in quantities that are greater than 10%, as film forming component. Hydrocolloids are necessary in order to facilitate the disgregation of the film but do not give the sensation of having a clean mouth since they tend to gel in contact with saliva.

EP1689374 by the same applicant describes self-supporting films for releasing active ingredients for therapeutic or food use based on maltodextrin and a plasticizer, totally without hydrocolloids. These films quickly disgregate in the mouth and release the active ingredient in the oral cavity keeping the sensation of having a clean mouth that is indeed of pullulan-based films.

These films however have a drawback concerning their physical stability as they tend to harden over time.

SUMMARY OF THE INVENTION

It has now been surprisingly found that it is possible to avoid hardening of the films based on maltodextrin and plasticizer by incorporating, in the composition, a homopolymer or copolymer of vinyl acetate.

The polymers in general of vinyl acetate and in particular polyvinyl acetate are insoluble in water, the latter being used in many medicinal products, for example in pharmaceutical formulations with a prolonged release over time, or as a base in chewing gum.

The present invention concerns orodispersible self-supporting films without hydrocolloids comprising:
  a) a film-forming substance consisting of a maltodextrin in a quantity comprised between 40 and 80% by weight;
  b) a plasticizer in a quantity comprised between 15 and 55% by weight;
  e) a surfactant system in a percentage comprised between 0.5 and 6% by weight;
  d) an active ingredient for food or therapeutic use in a quantity comprised between 0.05 and 30% by weight, characterised in that it contains a homopolymer or copolymer of vinyl acetate, in a quantity comprised between 2 and 10% by weight where the percentages are calculated on the total weight of said film.

DETAILED DESCRIPTION OF THE INVENTION

The orodispersible films of the invention have disgregation times evaluated in vitro that are lower than 3 minutes, they do not stick, they do not expand and are stable over time as far as the mechanical properties of elasticity and tensile strength are concerned.

The copolymer of vinyl acetate is preferably selected from the group consisting of polyvinylpyrrolidone vinyl acetate, ethylene vinyl acetate. More preferably the homopolymer of vinyl acetate, namely polyvinyl acetate, is used.

In particular the polyvinyl acetate used in the invention has an weight average molecular weight of between 5000 and 500000, preferably between 250000 and 450000. A polyvinyl acetate that can be used in the invention is that sold with trademark Kollicoat® SR 30D commercialised by BASF.

Preferably the content of polyvinyl acetate in the film according to the present invention is between 2.5 and 10%, more preferably between 3 and 10%, even more preferably between 3 and 6% and according to a particularly preferred solution between 3 and 5.5% by weight on the total weight of the film.

The maltodextrin used in the self-supporting film of the present invention has a dextrose content, expressed in equivalents, that is less than 50, and preferably is between 11 and 40.

The plasticizer used in the film of the present invention is preferably selected from the group consisting of polyalcohols, esters of citric acid, sebacic acid esters or mixtures thereof.

Particularly preferred are propylene glycol, glycerine, sorbitol, maltitol and mixtures thereof The surfactant system used in the film of the present invention consists of one or more surfactants, preferably selected from the group consisting of sorbitan derivatives, sorbitol derivatives, esters of sucrose, fatty acid esters and their mixtures.

The active ingredient for food use is preferably an active ingredient with a breath freshening action and/or indicated for oral hygiene, preferably eugenol or menthol or a vegetal extract or an active ingredient of natural origin, suitable for nutritional supplementation, preferably mineral salts among those normally used for such a purpose or one or more vitamins. According to a particularly preferred solution the vitamin is ascorbic acid.

The active ingredient for therapeutic use can be an ingredient with essentially topical action of the oral cavity selected from antibacterial, antifungal, antiviral agents or disinfectants of the oral cavity, or it can be an ingredient with an essentially systemic action selected from the group consisting of anti-inflammatory, analgesic, antipsychotic, hypnotic, anxiolytic, muscle relaxant, antimigraine, antiparkinsonian, antiemetic, antihistaminic, beta blocker, antiasthmatic anti-hypertensive, antitussive, laxative agents, inhibitors of type V phosphodiesterase, antikinetosis agents.

Active ingredients contained in such films are preferably selected from the group consisting of: Piroxicam, Ketoprofen, Diclofenac, Tramadol, Morphine, Nifedipine, Diazepam, Lorazepam, Alprazoiam, Bromazepam, Triazolam, Lormetazolam, Zolpidem, Paracetamol, Selegiline; Atenolol, Salbutamol, Sumatriptan, Clozapine, Ceterizine and their pharmaceutically acceptable salts.

Moreover, the films according to the invention can possibly contain other excipients selected in the class of non-stick substances like for example colloidal silica or talc, sweeteners, flavourings, colorants, preservatives, buffer systems or mixtures thereof.

The films object of the invention can be produced with known processes, like those described in EP 1689374.

In particular a process can be used comprising the steps of:
 i) dispersing the maltodextrin, the plasticizer, the surfactant system, the homopolymer or copolymer of vinyl acetate, preferably polyvinyl acetate and the active ingredient for therapeutic or food use in a polar solvent,
 ii) laminating the mixture obtained in the previous step on a silicone paper,
 iii) drying,
 iv) removing the silicone paper from the film obtained in the preceding step.

The polar solvent used in step (i) is preferably selected from water, water-mixable solvents or relative mixtures. According to a particularly preferred solution it consists of water. The temperature of the step itself, when the mixture of the aforementioned solvents is used, is preferably comprised between 60 and 105° C.

Example 1

Preparation of Placebo Orodispersible Films

The polymer mixture used for preparing the films was obtained by solubilizing maltodextrin DE 6 in a suitable amount of water kept at T=80° C.

The mixture was subsequently gradually cooled and glycerine, the surfactants, the homopolymer or copolymer of vinyl acetate and the other components were added in the ratios indicated in Table 1. The system obtained is kept under stirring until all the components were dissolved.

The composition of the polymer mixtures used for preparing the film is shown in Table 1.

TABLE 1

| Components | Composition %(w/w) | | | | | | | | | | |
|---|---|---|---|---|---|---|---|---|---|---|---|
| | 1 | 2 | 3 | 4 | 5 | 6 | 7 | 8 | 9 | 10 | 11 |
| maltodextrin DE6 | 78.99 | 80.72 | 76.50 | 74.87 | 70.78 | 62.68 | 76.50 | 76.00 | 77.00 | 76.50 | 75.00 |
| glycerine | 18.05 | 14.57 | 17.48 | 17.11 | 16.17 | 14.32 | 17.50 | 17.00 | 16.50 | 17.50 | 17.00 |
| Span80 | 2.96 | 3.71 | 3.01 | 3.01 | 3.05 | 2.99 | 3.00 | 3.00 | | 3.00 | 3.00 |
| PVAc | | 1.00 | 3.01 | 5.01 | 10.00 | 20.00 | | | | | |
| Capryol 90 | | | | | | | | | 3.00 | | |
| EVA | | | | | | | 3.00 | 4.00 | 3.50 | | |
| PVP/VA | | | | | | | | | | 3.00 | 5.00 |

The preparation of the film was carried out using the Mathis Labcoater-Labdryer model LTE —S (M) (CH) according to a method that foresees coating the mixture on a protective silicone sheet. The operation conditions used are as follows:

Coating speed: 1 m/min

Drying time: 15 min

Drying temperature: 60° C.

Rotation speed of the fan: 1800 rpm (revs/minute)

Coating thickness: 380 μm

The films thus prepared were separated by the protective sheet, cut with the desired dimensions and preserved in waterproof and lightproof packets.

Example 2

Determination of the Tensile Properties

The analysis of the tensile properties was carried out in accordance with ASTM standards (International Test Method for Thin Plastic Sheeting) (D 8 82-02) using an Acquati electronic dynamometer mod. AG/MC1 (I) on which a load cell of 5 N was assembled. The result of the tests is expressed as an average of the analysis on 5 samples for each formulation. The film was preliminarily cut into strips with a length of 100 mm and width of 12.5 mm. Once it was verified that there were no breaks or a lack of homogeneity in the matrix, the samples were positioned longitudinally between two pneumatic clamps spaced at 60 mm from one another. The separation velocity of the clamps was set at 500 mm/min. The test was considered finished once the film broke. Variations in the rigidity of the material were measured by determining the elastic modulus (Y) after the preparation of the films and after three months of preservation at 40° C.

The addition of PVAc was considered positive if the value Y increased at the moment of the preparation with respect to the formulation free from this component and if the variation of this value (V) after 3 months from the preparation did not vary more than 25%

Results

The elastic modulus values Y are shown in Table 2

TABLE 2 films 1-6 elastic modulus values after preparation thereof
and after being preserved for three months at 40°
C. and variation percentage (V) thereof over time.

| Formulation | Preservation (months) | | |
|---|---|---|---|
| | 0 | 3 | (V) |
| 1 | 26 | 61 | 135% |
| 2 | 59 | 78 | 32% |
| 3 | 113 | 119 | 5% |
| 4 | 55 | 69 | 25% |
| 5 | 35 | 40 | 14% |
| 6 | 14 | 23 | 64% |

The results show how the addition of PVAc in the range 3-10% makes it possible to improve the mechanical properties of the film. Indeed, with respect to the reference formulation 1, the films containing PVAc in the selected range make it possible to increase the values of Y and at the same time reduce the variation (V) of such a parameter Y over time.

Example 3

Preparation of Orodispersible Films Containing Diclofenac

Preparation of the Film

The films, the composition of which is shown in Table 3 were prepared according to what is described in example 1

Determination of the Mechanical Properties

The elastic modulus was determined according to what is described in Example 1.

Disgregation Test

The disgregation test was carried out according to, the specifications for orodispersible tablets shown in Eur. Ph. Ed. 7.0, setting the time T<3 min and using samples of 6 cm².

For every formulation, three tests were carried out and the results were expressed as an average±standard deviation.

Dissolution Test

The dissolution test in vitro was carried out on samples of 6 cm² using "Basket Dissolution Apparatus" (Eur. Ph. 7.0, Section 2.9.3).

The following parameters characterise the method used for evaluating the % drug dissolved:
  Equipment: Sotax AT7 Smart Dissolution system with Basket
  Temperature: 37±0.5° C.
  Dissolution medium: phosphate buffer pH 6.8
  Volume of dissolution: 500 mL
  Rotation speed: 100 rpm (revs/minute)
  Sampling time: 5 minutes The buffer volume described was inserted in the 7 vessels of the dissolution system and the system was left to settle at the set temperature of 37° C. A film was introduced in each of the first 6 baskets, the 7$^{th}$ vessel was used as the control and therefore the relative basket was kept empty.

Once the set temperature was reached, the baskets were lowered into the dissolution medium. After 5 minutes an aliquot was taken from each vessel. The samples obtained were analysed in HPLC by using the following method.

HPLC Agilent 1100, with Grace Alitima HP C 18 column with dimensions 100×4.6 mm and 3 μm. An isocratic elution was carried out comprising mixing a mobile phase A and a mobile phase B. Phase A consisted in 90% of a 20 mM phosphate buffer at pH 2.0 prepared dissolving 3.12 g of sodium dihydrogen phosphate in 1 litre of Milli-Q water and regulating the pH to 2.0 with conc. phosphoric acid ($H_3PO_4$) and 10% of tetrahydrofuran for HPLC. Phase B consisted of grade HPLC Methanol. The two phases were mixed in the proportions indicated here: Phase A: 40%, Phase B: 60%. The column temperature was set at 40° C., flow 1.3 ml/min, selected wavelength 254 nm, injection volume 2 μl.

Results

The results shown in table 3 indicate that the addition of PVAc makes it possible to obtain films having mechanical properties and tensile strength that are considerably higher than reference films, while maintaining unaltered disgregation and release characteristics.

TABLE 3

Composition and technological characteristics of the films

| | Formulation | |
|---|---|---|
| Components | D1 | D2 |
| Maltodextrin IT6 | 57.11 | 60.73 |
| Glycerine | 3.80 | 4.04 |
| Span 80 | 1.44 | 1.53 |
| PVAc 5,00 | 5.00 | — |
| sorbitol | 6.66 | 7.08 |
| Peach aroma | 3.42 | 3.64 |
| Betaine | 2.78 | 2.95 |
| Mint aroma in PG | 1.90 | 2.02 |
| Sucralose | 1.14 | 1.21 |
| Tween 20 | 0.72 | 0.77 |
| Titanium dioxide | 0.23 | 0.24 |
| Diclofenac epolamina | 15.80 | 15.78 |
| Mechanical properties Y(kPa) | 160 | 118 |
| Dissolution test % dissolved (limit >80%) | 98.6 | 104.5 |
| Disaggregation test T < 3 min | passed | passed |

Example 4

Preparation of Orodispersibile Films Containing Diclofenac Preparation of the Films The films D1 and D2 of the example 3 were preserved at 25° C. for 9 months and thus characterised according to the methods shown in the previous examples. In particular the elastic modulus was determined according to what is described in Example 1, whereas the disgregation time was verified according to what is described in Example 3.

Results

The results are shown in Table 4.

TABLE 4

Composition and technological characteristics of the films

| | Formulation | |
|---|---|---|
| | D1 | D2 |
| Mechanical properties Y (kPa) | 172 | 173 |
| Disaggregation test T < 3 min | Passed | Passed |

From the results shown above it is possible to highlight that the formulation D1 has a variation V % of Y after 9 months equal to 7.5%. On the other hand, the formulation without polyvinyl acetate has a variation % of Y of 46.6% much greater than the threshold limit of 25%.

The invention claimed is:

1. An orodispersible self-supporting film free from hydrocolloids comprising:
   a) a film-forming substance consisting of a maltodextrin in an amount between 40 and 80% by weight;
   b) a plasticizer in an amount between 15 and 55% by weight;
   c) one or more surfactants in an amount comprised between 0.5 and 6% by weight and;
   d) an active ingredient for food or therapeutic use in an amount between 0.05 and 30% by weight, said orodispersible self-supporting film free from hydrocolloids further containing a homopolymer or a copolymer of vinyl acetate in a quantity between 1 and 20% by weight, where the percentages are based on the total weight of said film.

2. The orodispersible self-supporting film according to claim 1 wherein the homopolymer or copolymer of vinyl acetate is polyvinylpyrrolidone vinyl acetate or polyvinyl acetate in a quantity between 1 and 10% by weight.

3. The orodispersible self-supporting film according to claim 2, wherein the polyvinyl acetate has a weight molecular weight average between 5000 and 500000.

4. The orodispersible self-supporting film according to claim 3 wherein the polyvinyl acetate has a molecular weight average between 250000 and 450000.

5. The orodispersible self-supporting film according to claim 1, wherein the homopolymer or copolymer of vinyl acetate is contained in an amount between 2.5 and 10% by weight based on the film total weight.

6. The orodispersible self-supporting film according to claim 5, wherein the homopolymer or copolymer of vinyl acetate is contained in an amount between 3 and 10% by weight based on the film total weight.

7. The orodispersible self-supporting film according to claim 5, wherein the homopolymer or copolymer of vinyl acetate is contained in an amount between 3 and 6% by weight based on the film total weight.

8. The orodispersible self-supporting film according to claim 7, wherein the homopolymer or copolymer of vinyl acetate is contained in an amount between 3 and 5.5% by weight based on the film total weight.

9. The orodispersible self-supporting film according to claim 1, wherein the maltodextrin has a dextrose content, expressed in equivalents, of less than 50.

10. The orodispersible self-supporting film according to claim 9, wherein the dextrose content is between 11 and 40.

11. The orodispersible self-supporting film according to claim 1, wherein the plasticizer is selected from the group consisting of polyalcohols, citric acid esters, sebacic acid esters and mixtures thereof.

12. The orodispersible self-supporting film according to claim 11, wherein the plasticizer is selected from the group consisting of propylene glycol, glycerine, sorbitol, maltitol and mixtures thereof.

13. The orodispersible self-supporting film according to claim 1, wherein the one or more surfactants are selected from the group consisting of sorbitan derivatives, sorbitol derivatives, esters of sucrose, fatty acid esters and mixtures thereof.

14. The orodispersible self-supporting film according to claim 1, wherein the active ingredient for food use is an active ingredient with a breath freshening action or is indicated for oral hygiene or is a natural active ingredient suitable for nutritional supplementation.

15. The orodispersible self-supporting film according to claim 14, wherein said active ingredient for food use with a breath freshening action is selected from menthol and eugenol.

16. The orodispersible self-supporting film according to claim 14, wherein said natural active ingredient suitable for nutritional supplementation is chosen from mineral salts normally used for such purpose, and vitamins.

17. The orodispersible self-supporting film according to claim 16, wherein the vitamin is ascorbic acid.

18. The orodispersible self-supporting film according to claim 1, characterized in that the active ingredient for therapeutic use is chosen from active ingredients with essentially topical action.

19. The orodispersible self-supporting film according to claim 18, wherein the active ingredient for therapeutic use is chosen from antibacterial, antifungal, antiviral and disinfectants of the oral cavity.

20. The orodispersible self-supporting film according to claim 1, wherein the active ingredient for therapeutic use is selected from the group consisting of active ingredients with essentially systemic action.

21. The orodispersible self-supporting film according to claim 20, wherein the active ingredient with essentially systemic action is selected from the group consisting of anti-inflammatory, analgesic, antipsychotic, hypnotic, anxiolytic, muscle relaxant, antimigraine, antiparkinsonian, antihemetic, antihistaminic, beta blocker, anti-asthmatic, antihypertensive, and antitussive agent.

22. The orodispersible self-supporting film according to claim 21 wherein the active ingredient is selected from the group consisting of: Piroxicam, Ketoprofen, Diclofenac, Tramadol, Morphine, Nifedipine, Diazepam, Lorazepam, Alprazolam, Bromazepam, Triazolam, Lormetazolam, Zolpidem, Paracetamol, Selegiline, Atenolol, Salbutamol, Sumatriptan, Clozapine, Cetirizine, and their pharmaceutically acceptable salts.

23. The orodispersible self-supporting film according to claim 1, further containing one or more excipients selected from the group consisting of non-sticking agents, sweeteners, flavourings, colorants, preservatives, buffer systems and mixtures thereof.

24. The orodispersible self-supporting film according to claim 23, wherein the non-sticking agent is selected from the group consisting of colloidal silica and talc.

25. The orodispersible self-supporting film according to claim 1 for therapeutic or food use.

26. A process for the preparation of the self-supporting film according to claim 1, comprising the following steps:
   i) dispersing maltodextrin, plasticizer, one or more surfactants, homopolymer or copolymer of vinyl acetate, and active ingredient for therapeutic or food use in a polar solvent,
   ii) laminating on a silicone paper the mixture obtained in the previous step,
   iii) drying,
   iv) removing the silicone paper from the film obtained in the preceding step.

* * * * *